United States Patent
Ji et al.

(10) Patent No.: US 6,663,567 B2
(45) Date of Patent: Dec. 16, 2003

(54) SYSTEM AND METHOD FOR POST-PROCESSING ULTRASOUND COLOR DOPPLER IMAGING

(75) Inventors: Ting-Lan Ji, San Jose, CA (US); Glen McLaughlin, Saratoga, CA (US)

(73) Assignee: Zonare Medical Systems, Inc., Mountain View, CA (US)

( * ) Notice: Subject to any disclaimer, the term of this patent is extended or adjusted under 35 U.S.C. 154(b) by 42 days.

(21) Appl. No.: 10/101,661

(22) Filed: Mar. 19, 2002

(65) Prior Publication Data

US 2003/0181814 A1 Sep. 25, 2003

(51) Int. Cl.[7] .................................................. A61B 8/06
(52) U.S. Cl. ...................................................... 600/455
(58) Field of Search ........................ 600/437, 440–441, 600/443, 447, 453–456; 128/916; 73/602, 625–626

(56) References Cited

U.S. PATENT DOCUMENTS

| | | |
|---|---|---|
| 4,409,982 A | 10/1983 | Plesset et al. |
| 4,803,990 A | 2/1989 | Bonnefous et al. |
| 4,853,904 A | 8/1989 | Pesque |
| 5,119,342 A | 6/1992 | Harrison, Jr. et al. |
| 5,140,558 A | 8/1992 | Harrison, Jr. et al. |
| 5,278,757 A | 1/1994 | Hoctor et al. |
| 5,291,090 A | 3/1994 | Dias |
| 5,295,485 A | 3/1994 | Shinomura et al. |
| 5,483,963 A | 1/1996 | Butler et al. |
| 5,505,203 A | 4/1996 | Deitrich et al. |
| 5,667,373 A | 9/1997 | Wright et al. |
| 5,722,412 A | 3/1998 | Pflugrath et al. |
| 5,740,806 A | 4/1998 | Miller |
| 5,793,701 A | 8/1998 | Wright et al. |
| 5,817,024 A | 10/1998 | Ogle et al. |
| 5,839,442 A | 11/1998 | Chiang et al. |
| 5,860,930 A | 1/1999 | Guracar |
| 5,893,363 A | 4/1999 | Little et al. |
| 5,897,501 A | 4/1999 | Wildes et al. |
| 5,904,652 A | 5/1999 | Gilbert et al. |
| 5,905,692 A | 5/1999 | Dolazza et al. |
| 5,919,138 A | 7/1999 | Ustuner |
| 5,921,931 A * | 7/1999 | O'Donnell et al. ......... 600/441 |
| 5,925,967 A | 7/1999 | Toda |
| 5,964,709 A | 10/1999 | Chiang et al. |
| 5,970,025 A | 10/1999 | Cole et al. |
| 5,973,438 A | 10/1999 | Toda |
| 6,055,861 A | 5/2000 | Banta, Jr. et al. |
| 6,063,030 A | 5/2000 | Vara et al. |
| 6,089,096 A | 7/2000 | Alexandru |
| 6,113,545 A | 9/2000 | Chiao et al. |
| 6,126,608 A | 10/2000 | Kemme et al. |
| 6,135,961 A | 10/2000 | Pflugrath et al. |
| 6,139,498 A | 10/2000 | Katsman et al. |
| 6,174,286 B1 | 1/2001 | Ramamurthy et al. |
| 6,203,498 B1 | 3/2001 | Bunce et al. |
| 6,217,520 B1 * | 4/2001 | He et al. ..................... 600/467 |
| 6,238,346 B1 | 5/2001 | Mason |
| 6,241,675 B1 * | 6/2001 | Smith et al. ................. 600/443 |
| 6,251,073 B1 | 6/2001 | Imran et al. |
| 6,352,509 B1 * | 3/2002 | Kawagishi et al. ......... 600/443 |
| 6,511,426 B1 * | 1/2003 | Hossack et al. ............. 600/437 |

* cited by examiner

Primary Examiner—Francis J. Jaworski
(74) Attorney, Agent, or Firm—Carr & Ferrell LLP (57) ABSTRACT

A system for ultrasonic imaging that includes a comparator for comparing at least one Doppler parameter input to a threshold value and generating a first mask. The comparator has a threshold value associated with each Doppler parameter input. A spatial filter is coupled to the comparator and produces a second mask, and a classification operator is coupled to the spatial filter and generates a third mask. The classification operator can effectively compare a value of a given pixel to the value of any nearby neighboring pixels and reclassify any given non-majority pixel to a majority value of the nearby neighboring pixels. An embodiment of the invention further includes a multi-parameter generator that outputs at least one Doppler parameter. The multi-parameter generator has a functional relationship based on at least one Doppler parameter input and at least one of any of the masks. A second spatial filter is coupled to receive the Doppler parameter input.

48 Claims, 4 Drawing Sheets

SYSTEM AND METHOD FOR POST-PROCESSING ULTRASOUND COLOR DOPPLER IMAGING

CROSS-REFERENCE TO RELATED APPLICATIONS

Not Applicable.

BACKGROUND OF THE INVENTION

1. Field of the Invention

The present invention relates to ultrasonic imaging, and more particularly, to a method and apparatus for improving and enhancing Doppler ultrasonic images.

2. Description of the Background Art

Ultrasonic imaging is frequently used for a variety of diagnostic procedures because it is non-invasive, low cost, and has a fast response time. These qualities are especially valuable in medical fields where an added benefit is reducing or eliminating a patient's exposure to radiation. Typically, ultrasonic imaging is accomplished by first generating and directing an ultrasonic wave into a media under investigation, then observing any resulting waves that are reflected back from dissimilar tissues and tissue boundaries within the media under investigation. The resulting waves are received as signals. These received signals are then post-processed and imaged on a screen by plotting a spot whose intensity is proportional to the amplitude of a reflected wave from a given location. The location of a particular spot in an image is based upon a known transmission and re-radiation rate after an ultrasonic wave is pulsed into the media under investigation.

Color Doppler imaging is a version of ultrasonic imaging used in medical ultrasonic systems. Color Doppler imaging generates two-dimensional, color-mapped images for displaying a Doppler velocity (or energy, or both) of a patient's blood flow. Typically, a color image is derived from Doppler parameter data and is overlaid on a corresponding two-dimensional tissue image. This overlay allows the user to simultaneously view blood flow dynamics and underlying tissue structures.

Doppler parameter data can be detected and extracted from reflected ultrasonic pulses by practicing the following steps: 1) transmitting multiple ultrasonic pulses via a transducer to a media under investigation; 2) receiving any returned signals responsive to the transmitted multiple ultrasonic pulses; 3) generating, through a beamformer, a two-dimensional complex image with preserved phase information for each of the received ultrasonic pulses; 4) applying clutter filtering across consecutively generated complex images to remove signals from any stationary objects; and, 5) calculating Doppler parameter data at each sample point, through auto-correlation methods or other means, from consecutive complex images corresponding to the multiple ultrasonic pulses.

Once generated, the Doppler parameter data are normally post-processed. Post-processing prepares the raw Doppler parameter data for viewing on a final display device. Post-processing of Doppler parameter data typically includes:

using one or more thresholds to exclude any image samples from Doppler parameter data that correspond to any random noise or residual clutter;

optionally applying some image processing techniques (e.g., smoothing, noise reduction, etc.) to the Doppler parameter data; and, color mapping and scan conversion of the Doppler parameter data.

Prior art ultrasonic systems use one or more threshold values to sort, or classify, Doppler parameter data thereby separating image samples of moving targets of interest (e.g., blood flow) from the image samples of residual clutter or noise. For instance, a lower limit of a Doppler energy threshold, $E_T$, can be set to exclude any image samples having a Doppler energy smaller than $E_T$ from an image of Doppler energy. Similarly, a lower limit of a Doppler velocity threshold, $V_T$, can be established to remove any image samples whose absolute value of Doppler velocity is less than $V_T$ from an image of Doppler velocity. Other types of thresholds may also be applied to other types of Doppler parameter data. Further, various threshold types can be combined to identify any image samples that represent only a desired moving target, such as blood flow, in an image of Doppler velocity.

One of the shortcomings of this method is that image samples of two classes of Doppler parameter data (e.g., blood flow and clutter/noise) often have parameter space overlaps. Therefore, misclassifying a number of samples in each class is common. This misclassification results in either black holes (i.e., apparent stationary regions) in a blood flow region, or random Doppler noise (i.e., apparent moving targets of interest) in stationary tissue regions.

SUMMARY OF THE INVENTION

An embodiment of the invention is a system for Doppler ultrasonic imaging that includes a comparator for comparing at least one Doppler parameter input with a threshold value and outputting a result. The result is used as a first mask. The comparator has at least one threshold value associated with each Doppler parameter input. A spatial filter is coupled to the comparator for producing a second mask. A classification operator is coupled to the spatial filter for generating a third mask. The classification operator is capable of effectively comparing a value of a given pixel to a value of any nearby neighboring pixels and reclassifying any given non-majority pixel to a majority value of the nearby neighboring pixels. An embodiment of the invention further includes a multi-parameter generator for outputting at least one Doppler parameter. The multi-parameter generator has a functional relationship based on at least one Doppler parameter input and at least one of the masks. Furthermore, a second spatial filter is coupled to receive the Doppler parameter input.

A further embodiment of the invention is a method for Doppler ultrasonic image processing that includes comparing at least one Doppler parameter input with an associated threshold value and outputting a result based on the comparison. A first mask is generated using the result. A second mask is then generated by filtering the first mask with a spatial filter. The method classifies the second mask. A third mask is generated by classifying said second mask. The classifying step includes effectively comparing a value of a given pixel to a value of any nearby neighboring pixels and reclassifying any given non-majority pixel to a majority value of the nearby neighboring pixels. A multivariable function is used to output at least one Doppler parameter. The multivariable function is chosen to include a functionality based on at least one Doppler parameter input and at least one of the masks.

DETAILED DESCRIPTION OF THE INVENTION

Figure 1:
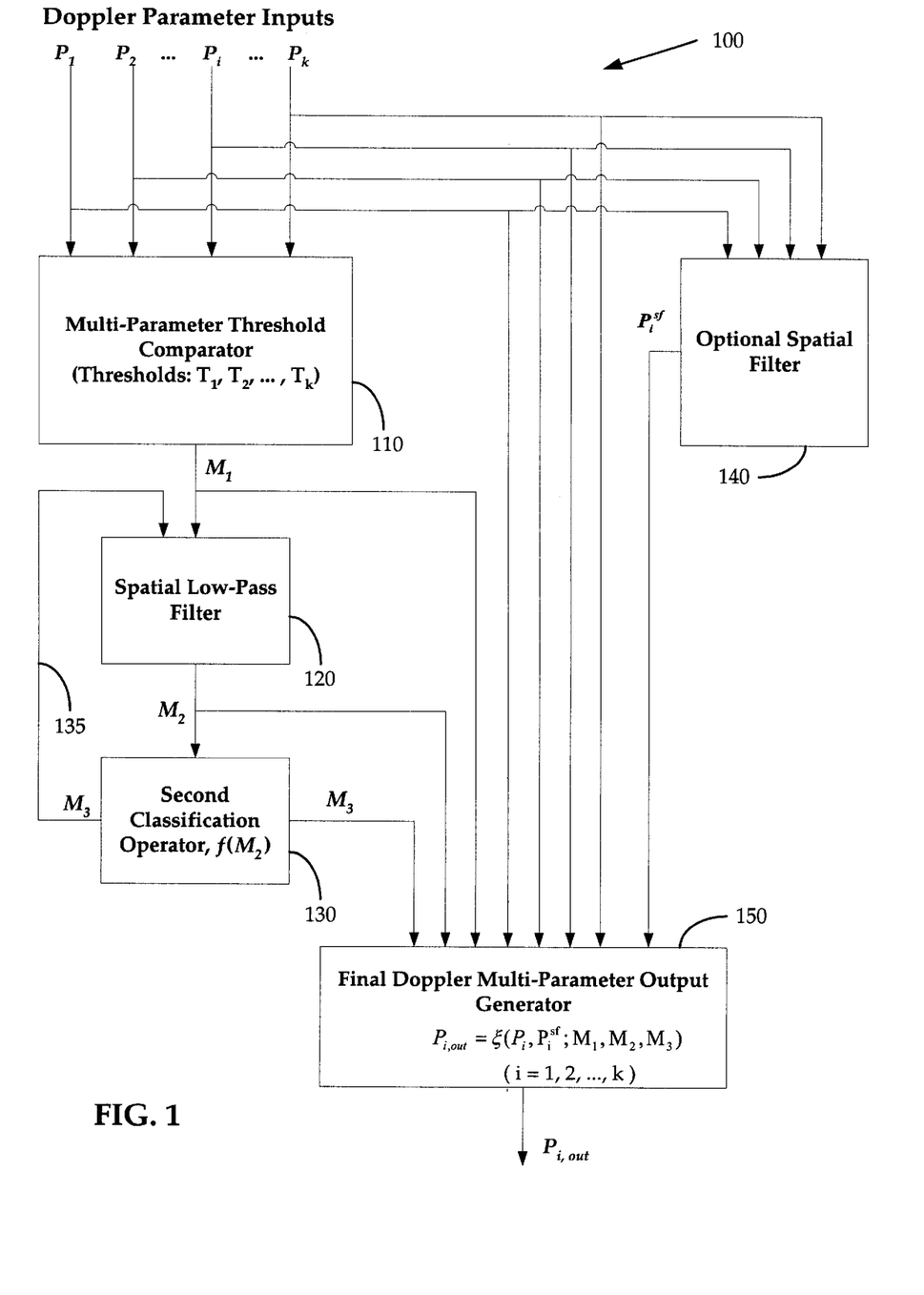
FIG. 1 shows an embodiment of a Doppler parameter post-processing system.

FIG. 1 shows a Doppler parameter post-processing system 100 in accordance with one embodiment of the invention. Among other things, the present invention uses multiple masking functions, mathematical combinations of these masking functions, and Doppler parameter inputs to classify various Doppler parameters of interest. Typical Doppler parameters of interest include, but are not limited to Doppler velocity, Doppler energy, and Doppler velocity variance of moving items such as blood flow, heart tissue, etc. Common misclassifications of prior art systems include black holes (i.e., apparent stationary regions) in a blood flow region, or Doppler noise (i.e., apparent moving parameters of interest) in stationary tissue regions. The present invention reduces these misclassifications.

An overview of an embodiment in accordance with FIG. 1 shows a plurality of Doppler parameter inputs and includes multiple classification and filtering modules. Specifically, FIG. 1 includes Doppler parameter inputs $P_1$ through $P_k$, final Doppler parameter output, $P_{i,out}$, multi-parameter threshold comparator 110 (i.e., the first classification operator), spatial low-pass filter 120, second classification operator 130, optional feedback loop 135, optional spatial filter 140, and final Doppler multi-parameter output generator 150.

In practice, the plurality of Doppler parameter inputs is routed to a multi-parameter threshold comparator 110. Multi-parameter threshold comparator 110 may also be used to combine a plurality of Doppler parameter inputs prior to comparing the combined Doppler parameter inputs to a threshold value. Optionally, Doppler parameter inputs may also be directed to an optional spatial filter 140, and a final Doppler parameter output generator 150. Each of these optional paths is discussed infra.

Multi-parameter threshold comparator 110 generates a first mask $M_1$. This first mask $M_1$ is either directed to a spatial low-pass filter 120, and optionally, may also be directed to final Doppler parameter output generator 150. After first mask $M_1$ is passed through spatial low-pass filter 120, a second mask $M_2$ is produced as an output of spatial low-pass filter 120. Second mask $M_2$ is directed to a second classification operator 130, and may also be directed to final Doppler parameter output generator 150. After second mask $M_2$ is passed through second classification operator 130, a third mask $M_3$ is produced as an output of second classification operator 130. Mask $M_3$ is either directed to final Doppler parameter output generator 150, and/or routed back, at least one more time, via an optional feedback loop 135, to the input of spatial low-pass filter 120. The third mask $M_3$ may again be filtered by spatial low-pass filter 120 and modified by second classification operator 130. The final Doppler multi-parameter output generator 150 performs a mathematical operation on any or all of the previously described masks, Doppler parameter inputs, and optionally filtered Doppler parameter inputs to produce a final Doppler parameter output, $P_{i,out}$, for each Doppler parameter of interest.

A more detailed inspection of the flow diagram in FIG. 1 shows multiple Doppler parameter inputs $P_1$, $P_2$, ..., $P_i$, ..., $P_k$ being routed to multi-parameter threshold comparator 110. Multi-parameter threshold comparator 110 compares each Doppler parameter, or a new parameter derived from more than one of the Doppler parameters, with an associated threshold level. Each threshold level has a pre-determined value associated with a given Doppler parameter or newly derived parameter. Results of comparisons performed by multi-parameter threshold comparator 110 are grouped in certain logical manners to generate first mask $M_1$. First mask $M_1$ may take the form of either binary outputs (0 or 1), or a normalized, continuous-tone output (e.g., any value between 0 and 1, inclusive).

In one exemplary embodiment, a given Doppler parameter input may be a Doppler velocity of blood flow in a media under investigation. If an absolute velocity of the Doppler velocity of blood flow for a pixel in a region of the media under investigation is above a given threshold level, then a binary output of "1" is assigned to that pixel in first mask $M_1$. Similarly, if the absolute value of velocity is below the given threshold, a binary output of "0" is assigned to that pixel in first mask $M_1$. The areas where a "0" is generated will mask data representing any low-velocity or stationary objects, thereby preventing such objects from appearing on a final display.

In another exemplary embodiment, a given Doppler parameter input may be a Doppler parameter energy of blood flow in a media under investigation. If the Doppler energy of blood flow for a pixel in a region of the media under investigation is above a given threshold level, then a binary "1" is assigned to that pixel in first mask $M_1$. Similarly, if the Doppler energy is below the given threshold, a binary output of "0" is assigned to that pixel in first mask $M_1$. The areas where "0's" are generated will mask data representing any low Doppler energy objects or noise, thereby preventing such objects from appearing on a final display.

Multi-parameter threshold comparator 110 outputs first mask $M_1$, which may be routed to spatial low-pass filter 120 and optionally, may also be directed to final Doppler multi-parameter output generator 150.

Spatial low-pass filter 120 may be, for example, a two-dimensional filter, an azimuth filter followed by a range filter, or a range filter followed by an azimuth filter. Spatial low-pass filter 120 is applied to first mask $M_1$ to affect certain aspects of first mask $M_1$. For example, application of spatial low-pass filter 120 to first mask $M_1$ may produce a smoothed second mask $M_2$. Such spatial low-pass filtering reduces the harsh and jagged boundaries and can also fill in small holes that might originally exist in first mask $M_1$.

Second mask $M_2$ is preferably routed to the second classification operator 130 to receive additional modification. In addition, second mask $M_2$ may optionally be directed to final Doppler multi-parameter output generator 150 where the second mask $M_2$ may be combined in some mathematical form with various other inputs.

Second classification operator 130 modifies second mask $M_2$ according to a chosen mathematical algorithm and a pre-determined threshold. The output of second classification operator 130 produces third mask $M_3$. Consequently, third mask $M_3$ can be considered as having a mathematical mapping from second mask $M_2$.

In one embodiment, second mask $M_2$ is compared to a threshold level. A value of this threshold level may or may not be the same as a value of a threshold level in multi-parameter threshold comparator 110. If second mask $M_2$ is above a given threshold level, for example, a threshold level of 0.5, then third mask $M_3$ is assigned a binary value of "1." Similarly, if second mask $M_2$ is below the threshold level of 0.5, then third mask $M_3$ is assigned a binary value of "0."

Optionally, third mask $M_3$ may be fed back to spatial low-pass filter 120 via optional feedback loop 135. In this case, third mask $M_3$ is again filtered prior to further processing.

Optional spatial filter 140 may be used to filter any of the Doppler parameter inputs. Optional spatial filter 140 may be a high-pass or low-pass spatial filter, a spatial bandpass filter, or a hybrid spatial multi-stage filter, for example. An output of optional spatial filter 140 produces a filtered Doppler parameter input, $P_i^{sf}$. Filtered Doppler parameter input $P_i^{sf}$ is routed directly into final Doppler multi-parameter output generator 150.

Any of the masks, Doppler parameter inputs, or filtered Doppler parameter inputs described may be combined in final Doppler multi-parameter output generator 150, which is the final step of post-processing in Doppler parameter post-processing system 100. Mathematically, a functional relationship for this final step of post-processing occurring in final Doppler multi-parameter output generator 150 may be written as $$P_{i,out} = \xi(P_i, P_i^{sf}; M_1, M_2, M_3)$$

where $P_i$ is any Doppler parameter input, $P_i^{sf}$ is any filtered Doppler parameter input, and $\xi()$ may be any arbitrary user-defined function. Any of the masks $M_1$ through $M_3$ may be combined with one or more Doppler parameter inputs $P_1$ through $P_k$ and filtered Doppler parameter inputs $P_i^{sf}$ to form final outputs. These outputs may be used, for example, to create Doppler parameter images.

This multi-stage classification operation of Doppler parameter post-processing system 100 results in more holes being filled in a region where a wanted Doppler parameter is classified (class A), less noise in a region where any unwanted signals from stationary targets are classified (class B), and a smoothing of borders between the two classes as compared to prior art systems and methods. Additional information may be obtained from combinations of the various masks. For example, any image samples exhibiting a change in class from first mask $M_1$ to third mask $M_3$ can be identified by ($M_3$–$M_1$). Such a mask combination technique indicates which, if any, image samples changed their classes during the embodiments described herein.

Figure 2:
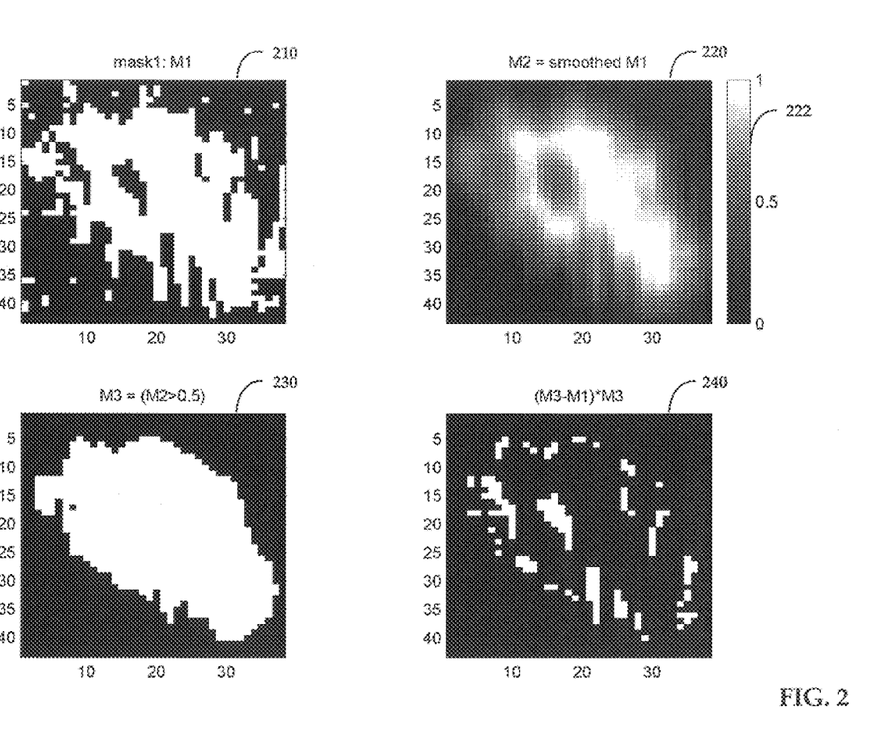
FIG. 2 shows a series of mask images generated through various filtering and classifications.

FIG. 2 shows an exemplary series of masks used for producing the final Doppler parameter images with varying levels of filtering. This series of masks could, for example, be produced using the system of FIG. 1.

First mask $M_1$ 210 is an exemplary output from multi-parameter threshold comparator 110. First mask $M_1$ 210 shows an area with arbitrary linear dimensional units along each axis. Black areas indicate a region where a Doppler parameter input (for example, the velocity of blood flow) was below a selected threshold level. White areas indicate a region where a Doppler parameter input was above a selected threshold level.

To generate a first mask $M_1$, each Doppler parameter input, or a new parameter derived from a combination of many Doppler parameter inputs, is compared interest. Two methods may be used to process the results of a comparison to generate a first mask $M_1$:

1) generate a binary output of a first classification from multi-parameter threshold comparator 110 as a first mask $M_1$; or
2) generate a non-binary or continuous-tone output by performing a threshold operation on one of the Doppler parameter inputs, $P_i$, to obtain a result of its threshold level comparison as a different first mask $M_1$.

Mathematically, a first mask $M_1$ of the first embodiment described in case 1) above can be written as $$M_1 = g(P_1, P_2, \ldots, P_i, \ldots, P_k; T_1, T_2, \ldots, T_i, \ldots T_k)$$

where $T_1, T_2, \ldots, T_i, \ldots T_k$ are the corresponding thresholds for Doppler parameter inputs $P_1, P_2, \ldots, P_i, \ldots, P_k$ and $g()$ indicates an arbitrary user-defined function. In this scenario, multiple Doppler parameter inputs are each compared to an associated threshold level.

For example, consider a first mask $M_1$ 210. A low-pass spatial filter is applied to the first mask $M_1$ 210 to obtain a smoothed version of first mask $M_1$ 210 producing a second mask $M_2$ 220. If there are fewer numbers of 0's than 1's in adjacent and nearby pixels of a given Doppler parameter input sample (a size of a nearby pixel neighborhood is determined by a kernel size of a spatial filter) in first mask $M_1$ 210, a value of the second mask $M_2$ 220 at that given Doppler parameter input sample will be larger than a threshold level. Otherwise, a value for a particular Doppler parameter input sample will be smaller than the threshold level. This means that the second mask $M_2$ 220 has a characteristic that any small "holes" (a few 0's surrounded by many 1's) originally appearing in first mask $M_1$ 210 will be filled, and any scattered "spikes" (a few 1's surrounded by many 0's) originally appearing in first mask $M_1$ 210 will be flattened, or reduced in overall value.

In the second embodiment described in case 2) above, first mask $M_1$ is not binary but may have a continuous tone range. This embodiment will produce an analog first mask that is quite different from first mask $M_1$ 210. An analog first mask $M_1$ is created using a gray-scale tonality range. An analog first mask $M_1$ may be used to emphasize particular aspects of Doppler parameter inputs not otherwise discernible using a binary first mask $M_1$. Analog first mask $M_4$ may also continue on to either or both of the two routes described previously for the binary version of first mask $M_1$.

Third mask $M_3$ 230 may be an output of second classification operator 130 (FIG. 1), modifying second mask $M_2$ 220. In this case, third mask $M_3$ 230 is a function of second mask $M_2$ 220 (i.e., $M_3 = f(M_2)$). One example of such a functional relationship, $f(M_2)$, is given by if $M_2 > 0.5$
  then $M_3 = 1$,
  else $M_3 = 0$ Using a mask such as third mask $M_3$ 230 reduces the likelihood of misclassification over prior art methods and systems by potentially reclassifying pixel samples in first mask $M_1$ based on information from nearby neighboring pixels.

Third mask $M_3$ could also be generally defined, for instance, as:

if $M_2 > M_t$
  then $M_3 = 1$,
  else $M_3 = 0$ where $M_t$ is a value of another threshold level. Consequently, a resulting third mask $M_3$ could conceivably be quite different from the third mask $M_3$ 230. For example, in another embodiment, a threshold value $M_t$ may be chosen to highlight a particular feature of interest (e.g., displaying only blood flow energies exceeding a given level or, in contrast, deliberately excluding high energy blood flow to view moving tissue, such as the movement of a heart valve).

Figure 3:
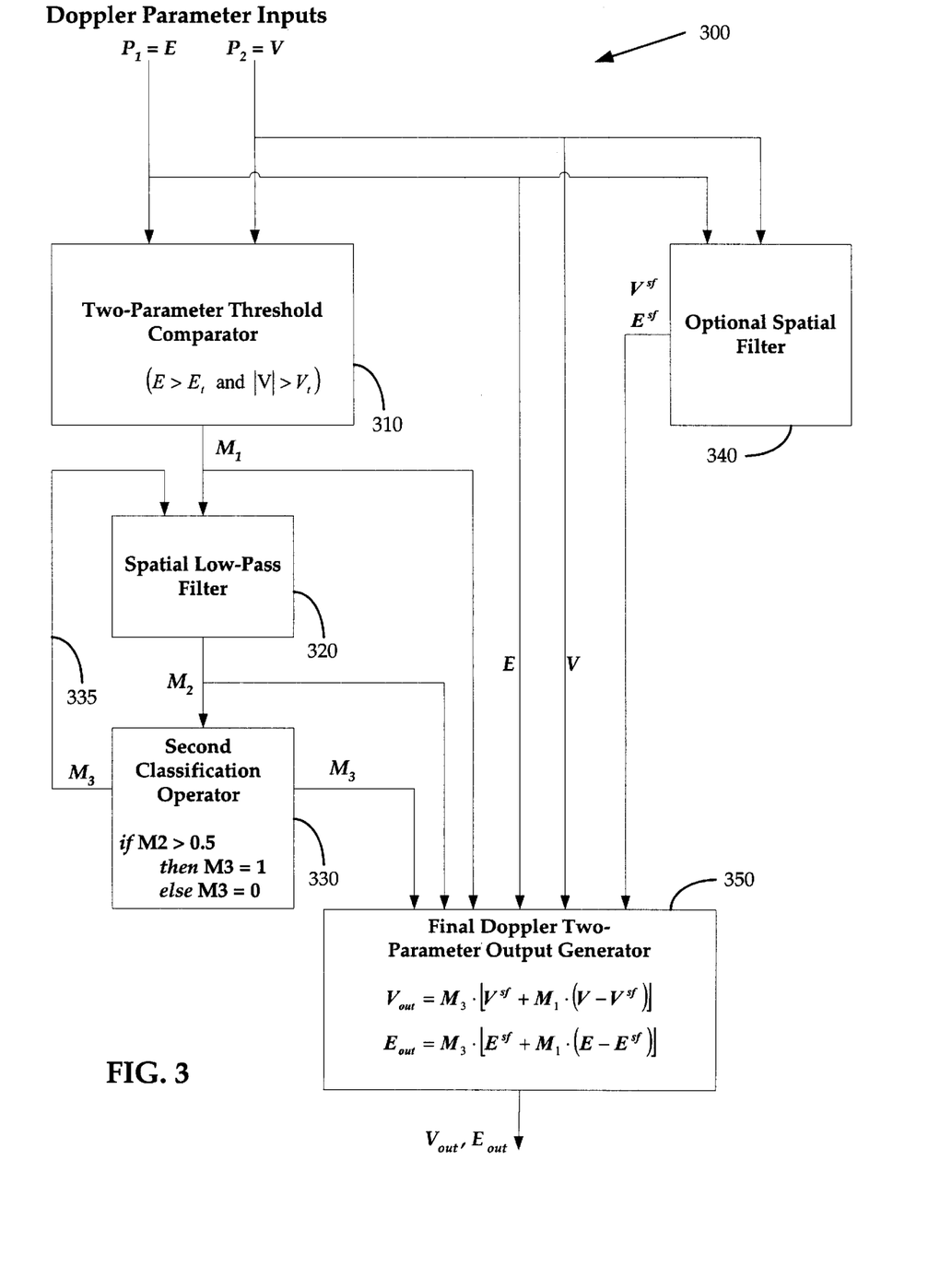
FIG. 3 shows another embodiment of a Doppler parameter post-processing system.

FIG. 3 shows another embodiment of the invention that generates a series of masks using various levels of filtering through Doppler two-parameter post-processing system 300. This embodiment includes Doppler parameter inputs $P_1$ and $P_2$, two-parameter threshold comparator 310, spatial low-pass filter 320, second classification operator 330, optional feedback loop 335, optional spatial filter 340, final Doppler two-parameter output generator 350, and masks $M_1$ through $M_3$.

In one embodiment, two Doppler parameter inputs, Doppler velocity, V, and Doppler energy, E, are selected as inputs to two-parameter threshold comparator 310. Two-parameter threshold comparator 310 compares each Doppler parameter input to an associated threshold level. A first mask $M_1$ is generated based on a comparison of values of each Doppler parameter input with the input's associated threshold level.

In one embodiment, the first mask $M_1$ could take the form of binary outputs (0 or 1) for various areas of the first mask $M_1$. In such a case, if a desired Doppler parameter is the Doppler velocity of blood flow for a particular small region of the media under investigation, and the threshold was set at 0.2, then a binary output of "1" would be generated for any velocity above 0.2. Likewise, a binary logic output of "0" would be generated for any velocity below 0.2. In areas where a "0" has been generated, low-velocity or stationary objects will be masked.

In another example, the Doppler parameter of interest could be an energy of blood flow. Energy of blood flow gives an indication of the amount of blood flow, as opposed to an actual velocity of blood flow. For instance, if a blood flow is perpendicular to the ultrasonic wave pulse, then the velocity of blood will be unknown, but still contains energy in the form of flowing blood. In such a case, a Doppler parameter input of energy may be compared to a threshold level in two-parameter threshold comparator 310. The velocity and energy threshold levels may be the same value or different values.

Once generated, the first mask $M_1$ may be routed to the inputs of both spatial low-pass filter 320 and final Doppler two-parameter output generator 350. Spatial low-pass filter 320 may be the same or similar to the low-pass filter as described and discussed in connection with FIG. 1. Also, like the embodiment described and discussed in connection with FIG. 1, spatial low-pass filter 320 generates second mask $M_2$. Final Doppler two-parameter output generator 350 will be discussed infra.

In one embodiment, second mask $M_2$ is routed directly into second classification operator 330 to receive additional modification. Second classification operator 330 modifies second mask $M_2$ according to a mathematical algorithm. An output of second classification operator 330 is a third mask $M_3$, which has a mathematical relationship to second mask $M_2$.

In one embodiment, second classification operator 330 compares second mask $M_2$ to a threshold level. The value of this threshold level may or may not be the same value as the threshold level in two-parameter comparator 310. Using thresholding, if a particular area within second mask $M_2$ is above a given level, for example, a threshold level of 0.5, then that area in third mask $M_3$ receives a binary value of "1." Similarly, if an area within second mask $M_2$ is below a threshold level of 0.5, then that area in third mask $M_3$ receives a binary value of "0." This type of comparison takes place for each of the two Doppler parameter inputs of energy and velocity.

Optionally, third mask $M_3$ may be fed back to spatial low-pass filter 320 via optional feedback loop 335. In such a case, third mask $M_3$ is again filtered prior to further processing.

Optional spatial filter 340 may receive and modify each of the Doppler parameter inputs directly. Optional spatial filter 340 may take the form of a high-pass or low-pass spatial filter, a spatial bandpass filter, or a hybrid spatial multi-stage filter, for example. An output of optional spatial filter 340 produces filtered Doppler parameter inputs, $V^{sf}$ and $E^{sf}$, for filtered Doppler velocity and filtered Doppler energy respectively. Filtered Doppler parameters $V^{sf}$ and $E^{sf}$ are routed directly into final Doppler two-parameter output generator 350.

Any of the masks, Doppler parameter inputs, and/or filtered Doppler parameter inputs described may be combined in final Doppler two-parameter output generator 350. The mask combinations may be combined according to a mathematical function or combined in some way with one or both Doppler parameter inputs and filtered Doppler parameter inputs to form final outputs. These outputs are used for creating Doppler parameter images of blood flow velocity and blood flow energy.

In one embodiment, a mathematical functional relationship between the output and inputs to final Doppler two-parameter output generator 350 may be expressed as $$V_{out} = M_3 \cdot [V^{sf} + M_1 \cdot (V - V^{sf})]$$

where $V^{sf}$ is a smoothed version of V obtained through optional spatial filter 340. Similarly, an exemplary algorithm for $E_{out}$ may be written mathematically as $$E_{out} = M_3 \cdot [E^{sf} + M_1 \cdot (E - E^{sf})]$$

where $E^{sf}$ is a smoothed version of E, again obtained through optional spatial filter 340.

In another embodiment using the FIG. 3 Doppler two-parameter post-processing system 300, another first mask $M_1$ may be defined as an output of Doppler two-parameter threshold comparator 310 produced from a functional relationship of Doppler parameter inputs of velocity, V, and energy, E, where velocity threshold level, $V_t$, and energy threshold level, $E_{t1}$; or $M_1 = g(V, E, V_t, E_{t1})$ are defined such that if $(|V| > V_t$ and $E > E_{t1})$
then $M_1 = E$,
else $M_1 = 0$ where $E_1$ is a first Doppler energy threshold. In this embodiment, first mask $M_1$ will take on a value equal to the Doppler parameter input of energy, E, if and only if both an absolute value of velocity and a value of energy are higher than each parameters' respective threshold level.

In one embodiment, first mask $M_1$ is filtered with spatial low-pass filter 320, which generates second mask $M_2$. Once generated, second mask $M_2$ represents a post-threshold, smoothed Doppler parameter input of energy and has an improved signal-to-noise ratio over the original Doppler parameter inputs. A third mask $M_3$ may be defined as an output of second classification operator 330 according to an algorithm if $M_2 > E_{t2}$
then $M_3 = 1$,
else $M_3 = 0$ where $E_{t2}$ is a value of a second energy threshold level. In one embodiment, improved results may be obtained where the value of $E_{t2}$ is set lower than $E_{t1}$. Once again, third mask $M_3$ may be fed back to spatial low-pass filter 320 via optional feedback loop 335, where it may again be filtered prior to further processing. Otherwise, third mask $M_3$ is routed to final Doppler two-parameter output generator 350.

In another embodiment, the output of final Doppler two-parameter output generator 350 may be mathematically expressed as $$V_{out}=M_3\cdot[V^{sf}+\alpha(M_2)\cdot(V-V^{sf})]$$

where $\alpha(M_2)$ is a function of mask $M_2$ with its value ranging between 0 and 1. Function $\alpha(M_2)$ may be selected such that when mask $M_2$ is low (but still greater than $E_{r2}$) $\alpha$ is approaching zero and when mask $M_2$ is high, $\alpha$ is approaching one.

Figure 4:
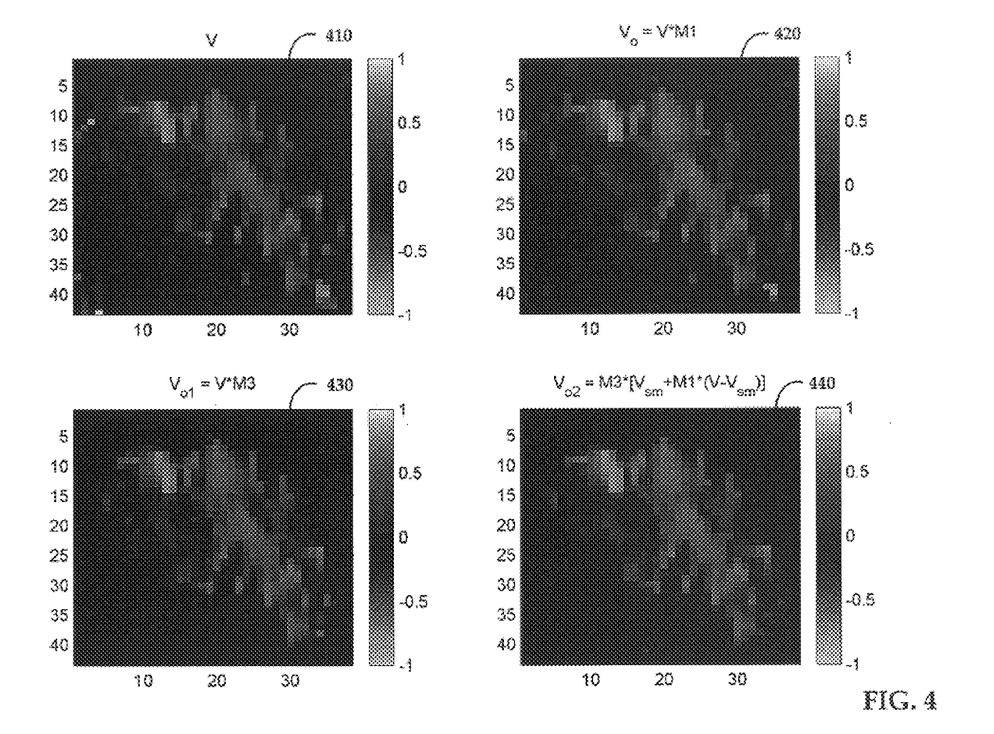
FIG. 4 shows a series of velocity images generated with different embodiments of this invention.

FIG. 4 shows a series of Doppler velocity image data outputs at various stages of processing. An image of Doppler parameter input of velocity 410 is raw, unfiltered data. Doppler parameter input of velocity 410 includes Doppler color noise in an area surrounding a non-discernible blood vessel boundary. FIG. 4 images 420, 430, and 440 are produced from various other masks to be described and explained infra. The Doppler color noise obfuscates the blood vessel boundary. However, notice that through the progression of these images, it is progressively easier to differentiate between the blood vessel boundaries and the moving blood flow inside from the stationary surrounding objects.

A typical Doppler parameter input of velocity 410 masked with first mask $M_1$ is shown as 420 in FIG. 4. First mask $M_1$ is further spatially smoothed with spatial low-pass filter 320 to obtain second mask $M_2$. Third mask $M_3$ may be defined as an output of the following exemplary second classification operator 330 according to the algorithm if $M_2>0.5$
   then $M_3=1$,
   else $M_3=0$ Doppler parameter input of velocity 410 is combined with third mask $M_3$ in final Doppler two-parameter output generator 350. The result generated in final Doppler two-parameter generator 350 are data that may be used, for example, to generate an output image such as Doppler parameter velocity output image 430. Another resulting Doppler parameter velocity output image 440 illustrates the effect of combining Doppler parameter input of velocity 410 with a previously defined algorithm from final Doppler two-parameter output generator 350, namely, $V_{o2}=M_3\cdot[V^{sf}+M_1\cdot(V-V^{sf})]$. In each of these latter three Doppler parameter output images 420, 430, and 440, the movement of blood flow and its associated boundaries are enhanced over the raw, unfiltered image of Doppler parameter input of velocity 410.

From the description of the exemplary embodiments of the process and apparatus set forth herein, it will be apparent to one of ordinary skill in the art that variations and additions to the embodiments can be made without departing from the principles of the present invention. For example, it could be easy to envision a system whereby an entire three-dimensional (3D) volume could be displayed at once as a Doppler image, as opposed to a two-dimensional area. This three-dimensional embodiment may be accomplished by holography or some other means, for example. It would be an obvious extrapolation from the tenets of the two-dimensional masking system presented herein to construct a three-dimensional masking method and apparatus.

What is claimed is:

1. A system for ultrasonic image processing, comprising:
   a comparator for comparing at least one Doppler parameter input to a threshold value and outputting a result, said result used as a first mask;
   a spatial filter coupled to said comparator for producing a second mask;
   a classification operator coupled to said spatial filter for generating a third mask; and
   a multi-parameter generator coupled to said comparator, said spatial filter, and said classification operator for accepting any of said masks.

2. The system of claim 1, further comprising a second spatial filter coupled to receive said at least one Doppler parameter input.

3. The system of claim 2, wherein said second spatial filter is a spatial low-pass filter.

4. The system of claim 2, wherein said second spatial filter is a spatial high-pass filter.

5. The system of claim 2, wherein said second spatial filter is a spatial band-pass filter.

6. The system of claim 2, wherein said second spatial filter is a spatial multi-stage combination filter.

7. The system of claim 2, wherein said multi-parameter generator produces an output according to a functional relationship based on said at least one Doppler parameter input that is modified by said second spatial filter.

8. The system of claim 7, wherein said multi-parameter generator produces an output according to a mathematical combination on said at least one Doppler parameter input that is modified by said second spatial filter with at least one of any of said masks.

9. The system of claim 7, wherein said multi-parameter generator produces an output according to a mathematical combination on said at least one Doppler parameter input that is modified by said second spatial filter with said at least one Doppler parameter input.

10. The system of claim 1, wherein said threshold value is an adjustable value.

11. The system of claim 1, wherein said threshold value is a fixed value.

12. The system of claim 1, wherein said spatial filter is a spatial low-pass filter.

13. The system of claim 1, wherein said spatial filter is comprised of an azimuth filter and a range filter.

14. The system of claim 1, wherein said third mask is coupled to said spatial filter.

15. The system of claim 1, wherein said multi-parameter generator produces an output according to a functional relationship based on said at least one Doppler parameter input and at least one of any of said masks.

16. The system of claim 1, wherein said multi-parameter generator produces an output according to a mathematical combination on said at least one Doppler parameter input with at least one of any of said masks.

17. The system of claim 1, wherein said multi-parameter generator produces an output according to a weighting applied to each of said first, second, and third masks and to said at least one Doppler parameter input.

18. A method for ultrasonic image processing comprising:
   comparing at least one Doppler parameter input with an associated threshold value and outputting a result based on said comparison;
   generating a first mask using said result;
   generating a second mask by spatially filtering said first mask;
   generating a third mask by classifying said second mask; and
   applying a multivariable function to at least one of said masks to produce at least one Doppler parameter output.

19. The method of claim 18, wherein said at least one Doppler parameter input is spatially filtered through a second spatial filter.

20. The method of claim 19, wherein said second spatial filter comprises a spatial low-pass filter.

21. The method of claim 19, wherein said second spatial filter comprises a spatial high-pass filter.

22. The method of claim 19, wherein said second spatial filter comprises a spatial band-pass filter.

23. The method of claim 19, wherein said second spatial filter comprises spatial multi-stage filtering.

24. The method of claim 18, wherein said spatial filtering step filters said first mask using a spatial low-pass filter.

25. The method of claim 18, wherein said spatial filtering step filters said first mask using a spatial azimuth filter and a range filter.

26. The method of claim 18, further comprising the step of spatially filtering said third mask.

27. The method of claim 18, wherein said classifying is based on effectively comparing a given Doppler parameter input value with values of any nearby neighboring pixels.

28. The method of claim 18, wherein said associated threshold value may be chosen to emphasize a particular feature.

29. The method of claim 18, wherein said multivariable function is chosen to include a functionality based on said at least one Doppler parameter input.

30. The method of claim 19, wherein said multivariable function is chosen to include a functionality based on said at least one Doppler parameter input that is modified by said second spatial filter.

31. The method of claim 18, wherein said multivariable function includes a functionality based on at least one of any of said masks.

32. The method of claim 26, wherein said multivariable function includes a functionality based on said third mask being coupled to said spatial filter.

33. A system for ultrasonic imaging, comprising:
  a comparator for comparing at least one Doppler parameter input to a threshold value and outputting a result, said result used for generating a first mask, said comparator having at least one threshold value associated with each of said at least one Doppler parameter input;
  a spatial filter coupled to said comparator for producing a second mask;
  a classification operator coupled to said spatial filter for generating a third mask, said classification operator capable of effectively comparing a value of a given pixel to a value of any nearby neighboring pixels and reclassifying any given non-majority pixel to a majority value of said nearby neighboring pixels;
  a second spatial filter coupled to receive said Doppler parameter input; and
  a multi-parameter generator for outputting at least one Doppler parameter, said multi-parameter generator being coupled to said at least one Doppler parameter input, said comparator, said spatial filter, said classification operator, and said second spatial filter, and having a functional relationship based on at least one said Doppler parameter input and at least one of any of said masks.

34. The system of claim 33, wherein said multi-parameter generator has a functional relationship based on at least one said Doppler parameter input that is modified by said second spatial filter.

35. The system of claim 33, wherein said second spatial filter is a spatial low-pass filter.

36. The system of claim 33, wherein said second spatial filter is a spatial high-pass filter.

37. The system of claim 33, wherein said second spatial filter is a spatial band-pass filter.

38. The system of claim 33, wherein said second spatial filter is a spatial multi-stage combination filter.

39. The system of claim 33, wherein said spatial filter is a spatial low-pass filter.

40. The system of claim 33, wherein said spatial filter is comprised of an azimuth filter and a range filter.

41. The system of claim 33, wherein said third mask is coupled to said spatial filter.

42. A method for ultrasonic image processing comprising:
  comparing at least one Doppler parameter input with an associated threshold value and outputting a result based on said comparison;
  generating a first mask using said result;
  spatially filtering said first mask with a spatial filter and generating a second mask;
  classifying said second mask, said classifying including effectively comparing a value of a given pixel to a value of any nearby neighboring pixels and reclassifying any given non-majority pixel to a majority value of said nearby neighboring pixels;
  generating a third mask by classifying said second mask; and
  applying a multi-parameter function to output at least one Doppler parameter, said multivariable function being chosen to include a functionality based on said at least one Doppler parameter input and at least one of any of said masks.

43. The method of claim 42, wherein said at least one Doppler parameter input is spatially filtered through a second spatial filter.

44. The method of claim 42, wherein said spatial filtering step filters said first mask using a spatial low-pass filter.

45. The method of claim 42, wherein said filtering step filters said first mask using an azimuth filter and a range filter.

46. The method of claim 42, further comprising the step of coupling said third mask to said spatial filter.

47. The method of claim 42, wherein said threshold value is chosen to emphasize a particular feature.

48. The method of claim 42, wherein said multivariable function is chosen to include a functionality based on said at least one Doppler parameter input that is modified by said second spatial filter.

* * * * *